United States Patent [19]

Crain

[11] Patent Number: 4,601,699

[45] Date of Patent: Jul. 22, 1986

[54] IMPLANT DEVICE

[75] Inventor: Kenny K. Crain, Terre Haute, Ind.

[73] Assignee: International Minerals & Chemical Corp., Terre Haute, Ind.

[21] Appl. No.: 677,419

[22] Filed: Dec. 3, 1984

[51] Int. Cl.⁴ .......................................... A61M 31/00
[52] U.S. Cl. ............................................ 604/64; 604/60
[58] Field of Search ........................ 604/59, 60, 62, 64

[56] References Cited

U.S. PATENT DOCUMENTS

| | | | |
|---|---|---|---|
| 2,502,909 | 4/1950 | Wick et al. | 604/60 |
| 2,601,852 | 7/1952 | Wendt | 604/59 |
| 3,016,895 | 1/1962 | Sein | 604/60 |
| 3,744,493 | 7/1973 | Booher et al. | 604/60 |
| 4,086,914 | 5/1978 | Moore | 604/64 |
| 4,473,369 | 9/1984 | Lueders et al. | 604/250 |
| 4,531,938 | 7/1985 | Kaye et al. | 604/62 |

Primary Examiner—C. Fred Rosenbaum
Assistant Examiner—Michelle N. Lester
Attorney, Agent, or Firm—Wendell R. Guffey; Thomas L. Farquer

[57] ABSTRACT

A low cost implant device suitable for manufacture by high speed injection molding techniques is described. The implant device can be fabricated and assembled using only two parts, a plunger assembly and a plunger assembly housing. The plunger assembly housing is provided with a socket-like chamber for receiving a disposable flanged cartridge containing a solid medicament in pellet form. The cartridge also can be made by injection molding. The device is used for subcutaneously implanting the solid pellet medicament in an animal.

4 Claims, 6 Drawing Figures

IMPLANT DEVICE

BACKGROUND OF THE INVENTION

1. Field of the Invention

The present invention relates to a device for implanting solid medicaments such as anabolic agents, hormones, antibiotics, and the like, in pellet form, beneath the skins of animals. More particularly, the present invention relates to a low-cost, easily-manufactured device for ejecting a solid pellet medicament from a disposable, single dose, pellet-containing cartridge and subcutaneously implanting the pellet in an animal.

2. Description of the Prior Art

Devices have long been available for subcutaneously implanting solid pellet medicaments in animals. For example, hormone and anabolic pellets are used in cattle and poultry for stimulating improved growth and altering the development of fat deposits to produce tender and better flavored products. Generally, these implant devices include a plunger, which when activated pushes a solid pellet through a hollow needle; the needle having previously been inserted beneath the animal's skin. Some devices are designed analogously to hypodermic syringes, see for example, U.S. Pat. No. 3,016,895; U.S. Pat. No. 3,058,465; U.S. Pat. No. 3,744,493; U.S. Pat. No. 3,921,632; U.S. Pat. No. 4,086,914 and No. PCT/US82/00927; while others resemble a gun in structure, see, for example, U.S. Pat. No. 3,402,712; U.S. Pat. No. 4,077,406; U.S. Pat. No. 4,105,030; Canadian Pat. No. 455,838 and Australian Pat. No. 253,175.

Typically, such prior art implant devices are relatively expensive to manufacture and are constructed from numerous pieces so that they can be disassembled for replacement of worn and defective parts. Consequently, these prior art devices are designed to be used over and over again. Some applications, however, such as where only a relatively small number of cattle need occasional treatment, do not require a device designed for repeated use. Rather, a device that can be inexpensively manufactured and thrown away after only a limited number of uses would be quite advantageous in such circumstances. Preferably, the device would be designed so that it is simple to use for even a small user having a very small herd, yet flexible enough to accommodate users having substantially larger herds.

It is one object of the present invention to provide an implant device of the type resembling a hypodermic syringe that is simple to use.

It is another object of the present invention to provide an implant device that can be manufactured inexpensively, using conventional injection molding technology, and as a consequence, can be economically disposed after only a limited number of uses.

It is a further object of the present invention to provide an implant device which employs a throw-away cartridge containing a single dose of the solid medicament.

These and other objects of the present invention will become more clearly apparent from a consideration of the specification and appended claims.

SUMMARY OF THE INVENTION

The present invention pertains to a device for subcutaneously implanting a solid pellet in an animal comprising in combination (1) a molded plunger assembly housing of unitary construction, said housing including
  (a) a first tubular section with an enlarged bore having
    (i) a user-proximal rear end opening with substantially the same cross-section as said enlarged bore and
    (ii) an ejector rod guide positioned near the user-distal front end, and
  (b) a second tubular section with a reduced bore coupled to the user-distal front end of said first tubular section;
(2) a hollow needle coupled to said second tubular section;
(3) a plunger assembly axially slideable in said housing, said assembly including
  (a) a molded user-actuated plunger of unitary construction, dimensioned for slideable movement in said enlarged bore, extending through the opening at the user-proximal rear end of said first tubular section, and
  (b) an ejector rod dimensioned for slideable movement in said hollow needle and connected to the user-distal front end of said plunger, said ejector rod having a length sufficient to extend into the ejector rod guide when the plunger assembly is in its rear-most position and to extend through the hollow needle when the plunger assembly is in its forward-most position, and
(4) a socket-like cartridge receiving chamber positioned at the user-distal end of said first tubular section and extending into said section tubular section having a flange receiving portion and a tubular receiving portion for retaining a flanged, solid pellet-containing cartridge.

DETAILED DESCRIPTION OF THE INVENTION

The present invention is directed to a device resembling a hypodermic syringe for subcutaneously implanting a solid pellet medicament, such as an anabolic agent, a hormone, an antibiotic and the like in an animal. In accordance with this invention, the solid pellet is contained in a disposable, flanged cartridge. If desired the cartridge can be made resistant to tampering. This cartridge is inserted into an appropriately shaped socket-like chamber in the implant device and the pellet is ejected from the device by manipulating an appropriately configured plunger assembly.

Figure 1:
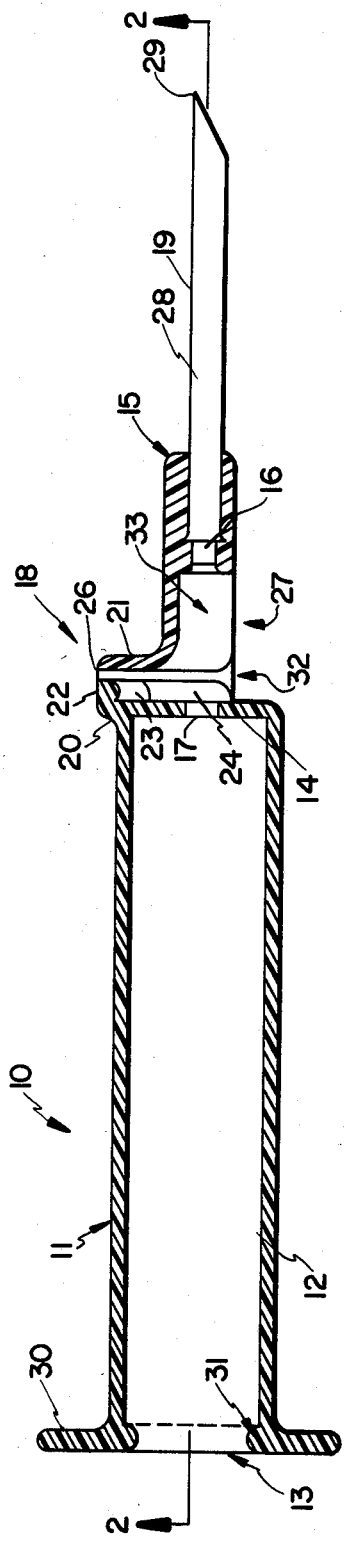
FIG. 1 is a cross-sectional view of the present invention showing the plunger assembly housing.
Figure 2:
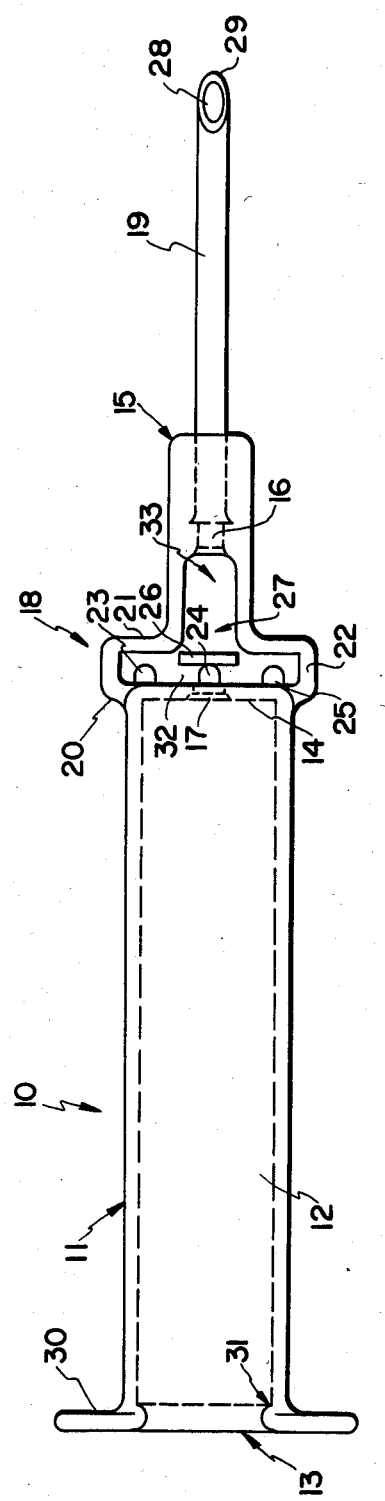
FIG. 2 is another cross-sectional view of the plunger assembly housing taken along line 2—2 of FIG. 1.

FIGS. 1 and 2 illustrate a suitable plunger assembly housing 10 constructed in accordance with the present invention. The housing 10 is if a unitary molded construction preferably manufactured by high speed injection molding and includes a first tubular section 11 with an enlarged bore 12 having an opening 13 with substantially the same cross section as said enlarged bore at the user-proximal rear end and an ejector rod guide 14 positioned at the user-distal front end. In the FIG. 1 design the ejector rod guide 14 comprises a plate or cap integral with and closing off the user-distal front end of the first tubular section 11. As shown, the rod guide is provided with a centrally located aperture 17.

Integrally coupled to the user-distal front end of the first tubular section 11 is a second tubular section 15 having a reduced bore 16. The axis of the second tubular section 15 is concentric with the first tubular section 11. In the FIG. 1 embodiment, the first tubular section is coupled to the second tubular section through a collar 18. Collar 18 forms a substantially semicircular torus concentrically positioned about the common axis of the first and second tubular sections and includes opposing flanges 20 and 21, which respectively are connected to the first and second tubular sections, and the interconnecting web 22. As shown, the second tubular section 20 extends outwardly from the flange 21. As will be described hereinafter, opposing flanges 20 and 21, rod guide 14 and connecting web 22 define a flange receiving portion 32 of a socket-like cartridge receiving chamber 27.

As noted above, the ejector rod guide 14 is provided with a centrally aligned aperture 17 located concentric with the axes of the first and second tubular sections. As shown more clearly in FIG. 2, the ejector rod guide also is provided with three parallel spaced ribs 23, 24 and 25 positioned on the outer (user-distal) surface of the ejector rod guide. These ribs help to define the flange receiving portion 32 of the socket-like cartridge receiving chamber 27 and their function will become more apparent in the following description.

Figure 6:
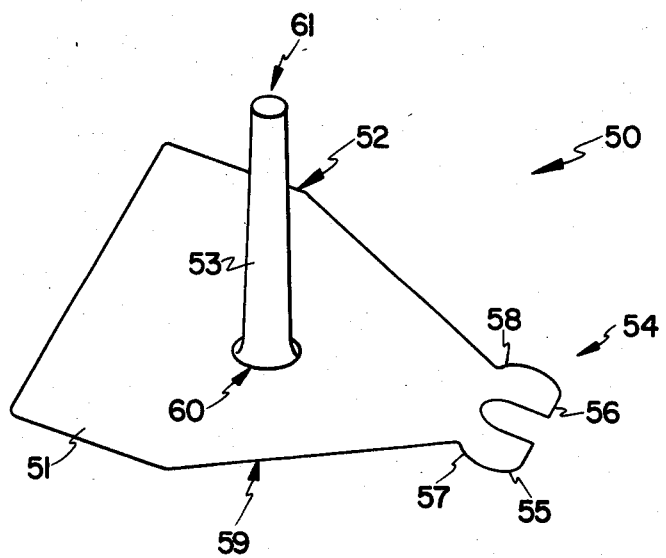
FIG. 6 is a perspective view of the flanged, solid pellet-containing cartridge of the present invention.

As shown in FIGS. 1 and 2, a socket-like cartridge receiving chamber 27 is positioned at the user-distal front end of the first tubular section 11 and axially extends into the second tubular section 15. The chamber 27 in effect constitutes a socket in a side wall of collar 18 and second tubular section 15. Ribs 23–25 on rod guide 14 in combination with flanges 20 and 21 and interconnecting web 22 form the flange receiving portion 32 of the socket-like cartridge receiving chamber 27 suitable for receiving a planar, flanged section of a pellet-containing cartridge. A suitably configured cartridge is shown in FIG. 6. The flanged cartridge is slidably inserted into this arrangement and is locked in place by cooperation between a locking means on the planar section of the flanged cartridge and the orifice 26 in the connecting web 22. At the same time, the tubular, pellet-retaining portion of the cartridge mates with the tubular receiving portion 33 of the chamber 27 in the second tubular section such that the axis of the tubular section of the cartridge is aligned with the axis of the reduced bore 16.

A hollow needle 19 is mounted on the user-distal end of the second tubular section 15. As shown in FIGS. 1 and 2, the hollow needle 19 preferably is coupled to the second tubular section 15 by embedding the needle permanently in the matrix of the second tubular section when the plunger assembly housing 10 is injection molded. The needle has a lumen 28 substantially the same as the cross-section of the ejector rod 41 (see FIG 3). The cross-section of lumen 28 is sufficient for receiving the solid pellet medicament ejected from the cartridge. The size (cross-section) of the needle may by varied in accordance with the size of pellets to be administered by the device, and the length of the needle can also be varied as needed. The hollow needle 19 also is provided with a puncture point 29 suitable for piercing the skin of an animal.

The user-proximal rear end of the first tubular section 11 is provided with handle means 30. Additionally, a ring-shaped protuberance 31, provided around the opening 13 at the user-proximal rear end of the first tubular section 11, slightly constricts the cross-section of the opening 13 and limits the outward movement of a plunger assembly position in bore 12. A plunger assembly is illustrated for example in FIG. 3.

Figure 3:
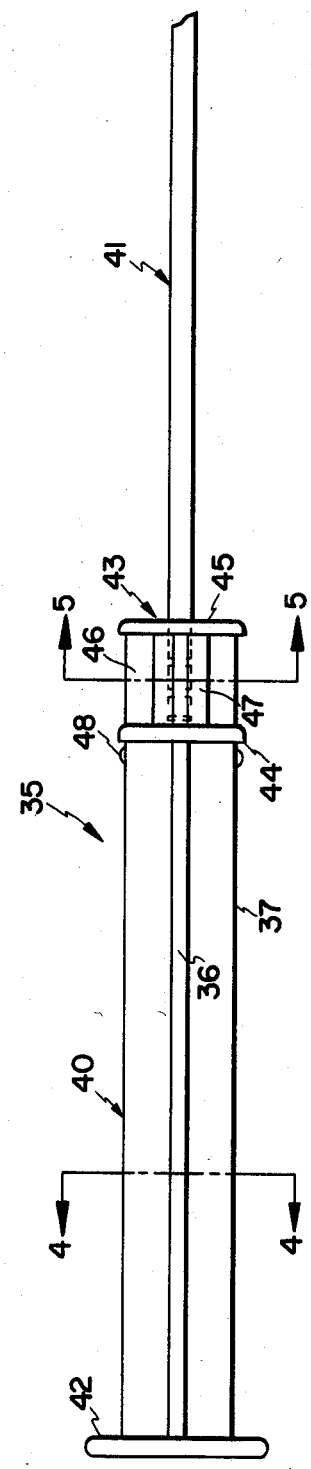
FIG. 3 is a cross-sectional view of the present invention showing the plunger assembly.
Figure 4:
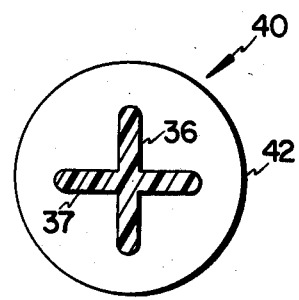
FIG. 4 is a cross-sectional view of the plunger taken along line 4—4 of FIG. 3.
Figure 5:
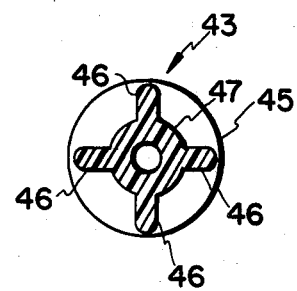
FIG. 5 is a cross-sectional view of the ejector rod support assembly taken along line 5—5 of FIG. 3.

Referring next to FIG. 3, a plunger assembly 35 is illustrated. Plunger assembly 35 includes a molded user-actuated plunger 40 of a unitary construction, preferably manufactured by high speed injection molding techniques, and an ejector rod 41 connected to the plunger 40 at its user-distal front end. As shown, the plunger 40 is constructed of two intersecting orthogonal beams 36 and 37 (shown more clearly in FIG. 4), and is dimensioned for slideable movement in the enlarged bore 12 of the first tubular section 11. The user-proximal rear end of the plunger 40 is provided with a plate 42 which during use is engaged by the thumb of the user. The user-distal front end of the plunger 40 is provided with an ejector rod support assembly 43 (see FIG. 5), consisting of spaced plates 44 and 45, struts 46 which connect the plates 44 and 45 and a central collar and support socket 47 adapted to receive and retain one end of the ejector rod 41. As shown, the ejector rod 41 is coupled to plunger 40 by embedding the rod permanently in the ejector rod support assembly 43 of plunger 40 when the plunger assembly is injection molded.

The ejector rod 41 is dimensioned for slideable movement in lumen 28 of hollow needle 19. The ejector rod has a sufficient length to extend into the ejector rod guide 14 when the plunger assembly is in its rear-most position and to extend through the hollow needle 19 when the plunger assembly is in its forward-most position. In this way, ejection of the solid pellet from a cartridge supported in the implant device is insured. In one embodiment, the user-distal front end of the ejector rod is chamfered, i.e., beveled, so as to facilitate passage of the ejector rod through the constricted rear opening of the disposable cartridge. For example, if the cartridge is sealed with foil, use of a camfered ejector rod prevents any tearing of foil pieces from the foil-backed cartridge during operation and thereby avoids forcing any foil through the hollow needle and beneath the animals skin with the solid pellet.

Once inserted into the plunger assembly housing 10, axial movement of the plunger assembly 35 in the housing is restricted under normal usage at its rear-mast position by the ring-shaped protuberance 31 and at its forward-most position by the ejector rod guide 14. Additionally, a locking dimple 48, positioned on the edge of a beam 36 and/or 37 of plunger 40 near the ejector rod support assembly 43, in cooperation with the ring-shaped protuberance 31, serves to lock temporarily the plunger assembly 35 as desired in its rear-most position.

A suitably designed flanged, pellet-containing cartridge 50 for use in connection with the plunger assembly housing 10 of FIGS. 1 and 2 is illustrated in FIG. 6. As shown, the cartridge 50 comprises a planar section 51 with a substantially perpendicularly aligned tubular section 52. The tubular section 52 has a bore 53 substantially the same as the cross-section of ejector rod 41. The bore 53 communicates with an opening 60 in said planar section 51 through which the solid pellet initially is inserted and an opening 61 through which the pellet subsequently is ejected. The bore 53 of tubular section 52 typically is sized so as to contain a single dose of a solid medicament in pellet form. A wide variety of pellet shapes are contemplated within the broad practice of this invention including both cylindrically-shaped and spherically-shaped pellets. The rear opening 60 through which the solid pellet initially is inserted into the cartridge is sealed so as to prevent premature release of the pellet from the cartridge. Opening 60 can be sealed completely, for example, by a foil membrane or partially sealed simply by deforming the base of the tubular section to restrict the area of the opening. The opening 61 is similarly restricted to prevent premature release of the pellet. In an alternate embodiment the opening 61 can be sealed completely with the plastic material used to mold the cartridge as described hereafter, and the seal broken just prior to use. Suitable seal designs for openings 60 and 61 will be readily apparent to those skilled in the art.

In the FIG. 6 embodiment, the planar section 51 of the cartridge is provided with a taper 59 patterned after the internal shape of collar 18 to facilate its insertion into the flange receiving portion of the socket-like cartridge receiving chamber 27. At the end of taper 59 a locking means 54 is provided. In this embodiment, the locking means 54 simply comprises spaced fingers 55 and 56 extending from the end of the flange 51. By fabricating the planar section 51 of the cartridge 50 from a flexible material such as high density polyethylene, polypropylene and the like, this configuration permits the fingers to undergo a pincer-like movement upon insertion through opening 26. The fingers could also be united at their ends to define a continuous loop defining, for example, an oval center. As long as constructed from suitably flexible material, e.g., polypropylene, this structure also can be deformed in a pincer-like manner for insertion through opening 26.

At the outer juncture of the locking means with the planar section 51 of cartridge 50 are notches 57 and 58 which cooperate with the opening 26 in connecting web 22 of collar 18 to lock the cartridge in place. When the flanged cartridge is inserted into the socket-like cartridge receiving chamber 27, the planar section 51 slideably engages ribs 23, 24 and 25 of rod guide 14 and flange 21 which define the flange receiving portion 32 of chamber 27 and the cartridge is locked into position when the locking means 54 extends through the opening 26 in web 22. Various other arrangements for locking cartridge 50 in place in cooperation with opening 26 will be readily apparent to one skilled in the art, for example, a tongue extending from the edge of cartridge 50 could be inserted through opening 26 and held in place by a variety of means. The tubular section 52 of the cartridge 50 mates with the tubular receiving portion 33 of the socket-like cartridge receiving chamber 27 which extends into the second tubular section 15. When locked into position, the axis of the cartridge is aligned with the axis of the plunger assembly, plunger assembly housing and the hollow needle.

The entire assembly, except for the hollow needle 19 and ejector rod 41, typically is molded from a plastic material such as nylon, polycarbonate, high density polyethylene, high density polypropylene, or other plastic material. Preferably a material eg. polypropylene capable of being injection molded at high speed is used. Typically, the needle 19 is fabricated from stainless steel, while the ejector rod 41 could either be injection molded with the plunger assembly or could be fabricated from stainless steel.

The implant device can be injection molded using techniques well known in the art. Typically, the implant device is molded in just two pieces i.e. the entire plunger assembly housing 10 with embedded needle 19 and the plunger 40 with the embedded ejector rod 41. By fabricating plunger 40 such that the diameter of the plates 44 and 45 of support assembly 43 are only slightly larger than the diameter of opening 13 defined by ring-shaped protuberance 31, these separate pieces then can be assembled into the final device simply by forcing the plunger assembly 35 (plunger 40) through the ring-shaped protuberance-restricted user-proximal opening 13 at the rear end of housing 10.

As noted above, the second tubular section 15 is injection molded directly around needle 19 so that the needle is held permanently in place. Similarly, the plunger 40 can be injection molded directly around the ejector rod 41. By using high speed injection molding techniques the implant device can be manufactured at low cost and therefore can be disposed economically after only a limited number of uses. The flanged cartridge 50 also is produced by injection molding techniques.

In use, a flanged, solid pellet-containing cartridge having the illustrated design is inserted into the socket-like cartridge receiving chamber 27 and locked into position by forcing fingers 55 and 56 through the opening 26 in the connecting web 22 of collar 18. The cartridge contains a single dose of a solid, pelleted medicament such as RALGRO ®, zeranol anabolic agent available from International Minerals and Chemical Corp. Upon placing the index finger and second finger about the handle 30 and the thumb on the plate 42 of plunger assembly 35, the needle 19 is inserted beneath the animal's skin and the user may manipulate the ejector rod 41 with the thumb so as to pierce the foil membrane of the cartridge and force the solid pellet through the hollow needle 19 and into the tissue of the animal.

While the device of the present invention has been described with respect to a preferred embodiment, it should be understood that various changes may be made without departing from the spirit and scope of the invention as particularly claimed below.

I claim:

1. A device for subcutaneously implanting a solid pellet in an animal comprising in combination
   (1) a molded plunger assembly housing of unitary construction, said housing including
      (a) a first tubular section with an enlarged bore having
         (i) a user-proximal rear end opening with substantially the same cross section as said enlarged bore and
         (ii) an ejector rod guide positioned near the user-distal front end, and
      (b) a second tubular section with a reduced bore coupled to the user-distal front end of said first tubular section;
   (2) a hollow needle embedded permanently in said second tubular section;
   (3) a plunger assembly axially slideable in said housing, said assembly including
      (a) a molded user-actuated plunger of unitary construction dimensioned for slideable movement in said enlarged bore, extending through the opening at the user-proximal rear end of said first tubular section, and (b) an ejector rod dimensioned for slideable movement in said hollow needle and embedded permanently in the user-distal front end of said plunger, said ejector rod having a length sufficient to extend into the ejector rod guide when the plunger assembly is in its rear-most position and to extend through the hollow needle when the plunger assembly is in its forward-most position, and (4) a socket-like cartridge receiving chamber positioned at the user-distal front end of said first tubular section and extending into said second tubular section having a flange receiving portion and a tubular receiving portion for retaining a flanged, solid pellet-containing cartridge.

2. A flanged, solid pellet-containing cartridge comprising a planar section with a substantially perpendicularly aligned tubular section extending outwardly therefrom, said tubular section having a sufficient cross-section to contain a solid pellet medicament, said planar section having an opening through which a pellet can be inserted into the tubular section and means for sealing said opening, the planar section constituting a flange for said tubular section and having a taper which terminates with a locking means, said taper facilitating insertion of the cartridge into an implant device of the type including (1) a molded plunger assembly housing of unitary construction, said housing including (a) a first tubular section with an enlarged bore having (i) a user-proximal rear end opening with substantially the same cross section as said enlarged bore and (ii) an ejector rod guide positioned near the user-distal front end, and (b) a second tubular section with a reduced bore coupled to the user-distal front end of said first tubular section;

(2) a hollow needle embedded permanently in said second tubular section;

(3) a plunger assembly axially slideable in said housing, said assembly including (a) a molded user-actuated plunger of unitary construction dimensioned for slideable movement in said enlarged bore, extending through the opening at the user-proximal rear end of said first tubular section, and (b) an ejector rod dimensioned for slideable movement in said hollow needle and embedded permannently in the user-distal front end of said plunger, said ejector rod having a length sufficient to extend into the ejector rod guide when the plunger assembly is in its rear-most position and to extend through the hollow needle when the plunger assembly is in its forward-most position, and (4) a socket-like cartridge receiving chamber positioned at the user-distal front end of said first tubular section and extending into said second tubular section having a flange receiving portion and a tubular receiving portion.

3. The device of claim 1 wherein said molded housing is fabricated from a plastic material selected from the group consisting of nylon, polycarbonate, polyethylene, and polypropylene.

4. The device of claim 1 wherein said molded plunger is fabricated from a plastic material selected from the group consisting of nylon, polycarbonate, polyethylene and polypropylene.

* * * * *

UNITED STATES PATENT AND TRADEMARK OFFICE
CERTIFICATE OF CORRECTION

PATENT NO. : 4,601,699

DATED : July 22, 1986

INVENTOR(S) : Kenny K. Crain

It is certified that error appears in the above-identified patent and that said Letters Patent are hereby corrected as shown below:

Column 2, line 66, "if" should read -- of --

Column 4, line 53, "rear-mast" should read -- rear-most --

Signed and Sealed this

Twenty-eighth Day of April, 1987

Attest:

DONALD J. QUIGG

Attesting Officer

Commissioner of Patents and Trademarks